United States Patent [19]

Hurson

[11] 4,133,081

[45] Jan. 9, 1979

[54] CLAMP

[76] Inventor: James K. Hurson, 14 Second St., Orangeville, Ontario, Canada

[21] Appl. No.: 734,930

[22] Filed: Oct. 22, 1976

Related U.S. Application Data

[62] Division of Ser. No. 492,208, Jul. 26, 1974, Pat. No. 4,048,987.

[30] Foreign Application Priority Data

Jun. 28, 1974 [CA] Canada .................................. 203740
Aug. 6, 1973 [GB] United Kingdom ............... 37278/73

[51] Int. Cl.² ............................................. A61B 17/02
[52] U.S. Cl. ..................................... 24/73 A; 128/20
[58] Field of Search ............. 24/73 A, 73 FA, 73 SA, 24/81 AD, 81 AE, 248 R, 243 R, 73, 81; 49/2, 208; 128/20

[56] References Cited

U.S. PATENT DOCUMENTS

| 697,908 | 4/1902 | Wilkin | 24/81 AE |
| 1,946,898 | 2/1934 | Carlson | 24/243 R |
| 3,309,052 | 3/1967 | Borisof | 24/73 SA |

Primary Examiner—Louis Rimrodt
Attorney, Agent, or Firm—Charles L. Gholz

[57] ABSTRACT

Disclosed is a clamp comprising a base, a first jaw mounted on the base, an opposing jaw spaced along the base from the first jaw, and clamp opening and closing means. The opposing jaw is pivotably mounted at one end to the base, and the clamp opening and closing means comprise a first elongated member pivotably mounted at one end on the base at a point remote from the jaws for pivotal movement about a first axis, a second elongated member pivotably mounted at one end on the opposing jaw at a point remote from the base for pivotal movement about a second axis and pivotably connected at its other end to the first elongated member at its other end for pivotal movement about a third axis, and a lever pivotably mounted on the third axis.

21 Claims, 3 Drawing Figures

CLAMP

This is a Division of application Ser. No. 492,208, filed July 26, 1974, now 4,048,987, Sept. 20, 1977.

FIELD OF THE INVENTION

This invention relates to clamps. It was developed as a clamp for a surgical retractor, but it is obviously not limited to holding a surgical retractor. It is a member of the class of clamps which employ toggle mechanisms, but it differs from and effects a significant improvement over all such clamps known to me.

SUMMARY OF THE INVENTION

Basically the present invention is a clamp comprising a base, a first jaw mounted on the base, an opposing jaw spaced along the base from the first jaw, and clamp opening and closing means. The opposing jaw is pivotably mounted at one end to the base, and the clamp opening and closing means comprise a first elongated member pivotably mounted at one end on the base at a point remote from the jaws for pivotal movement about a first axis, a second elongated member pivotably mounted at one end on the opposite jaw at a point remote from the base for pivotal movement about a second axis and pivotably connected at its other end to the first elongated member at its other end for pivotal movement about a third axis, and a lever pivotably mounted on the third axis. The total length of the first elongated member between the first and third axes and the second elongated member between the second and third axes exceeds the straight line distance between the first and second axes when the clamp is closed. Accordingly, when the opposing jaw is moved from its open position to its closed position by actuation of the lever, the third axis moves from a first position in which the third axis is on one side of an imaginary line connecting the first and second axes, through a position in which the third axis is on the imaginary line connecting the first and second axes, and to a position in which the third axis is on the other side of the imaginary line connecting the first and second axes. Preferably the first elongated member abuts the base when the opposing jaw is in its closed position so that the "over center" motion of the third axis causes the opposing jaw to be locked fixedly in its closed position. Preferably also the lever and the second elongated member are formed integrally and the lever abuts the first elongated member when the opposing jaw is in its closed position.

BRIEF DESCRIPTION OF THE DRAWING

Embodiments of the present invention will now be described, by way of example, with reference to the accompanying drawings.

DESCRIPTION OF PREFERRED EMBODIMENTS

Figure 1:
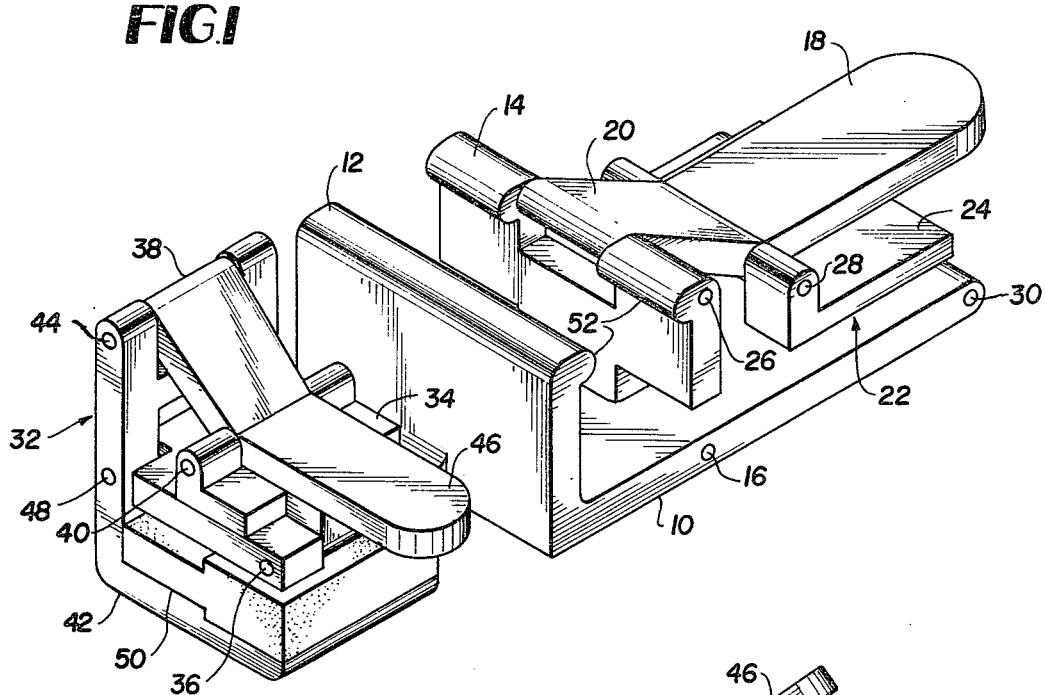
FIG. 1 is a perspective view of two embodiments of the subject invention mounted on a common base.
Figure 2:
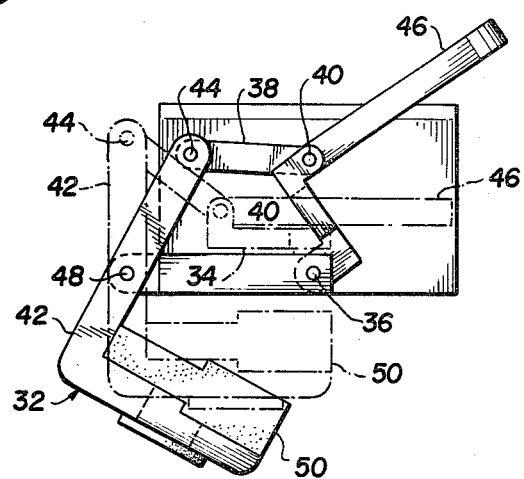
FIG. 2 is an end view of the apparatus of FIG. 1 showing one clamp open in solid line and closed in broken line.
Figure 3:
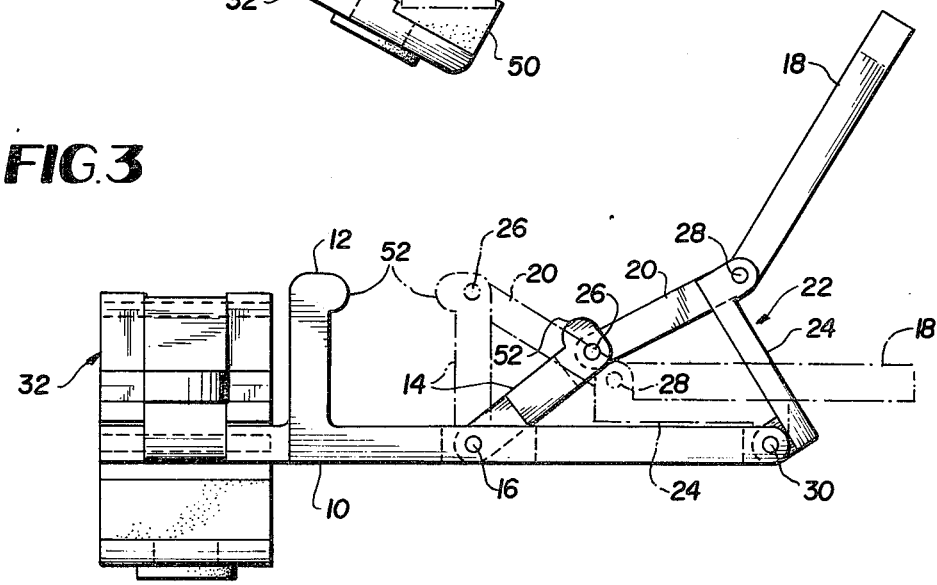
FIG. 3 is a side view of the apparatus of FIG. 1 showing the other clamp open in solid line and closed in broken line.

Referring now to the drawings, two clamps mounted on a common base are shown. The purpose of mounting the two clamps on a common base is so that one clamp can be used to clamp the device to a frame or other support (as illustrated in U.S. Pat. No. 4,048,987) while the other clamp is used to hold something else, such as the surgical retractor illustrated in that patent. However, the drawings also serve to illustrate two different embodiments of the subject clamp.

The device shown in the drawings comprises a base portion 10, a fixed jaw 12 extending upwardly from one end of the base portion 10, and a movable jaw 14 pivotally mounted at 16 on the base portion 10. The movable jaw 14 is moved between opened and closed positions by means of a lever 18 which is attached to one member 20 of a knee linkage 22 the other member of which is designated by the numeral 24. The member 20 is pivotally attached at 26 to the top of the jaw 14 and at 28 to the member 24, and the member 24 is pivotally attached at its other end at 30 to the base portion 10. The pivot 28 between the two members 20 and 24 of the knee linkage is moved over-center by actuation of the lever 18 either upwardly to open the clamp or downwardly to close the clamp. It will be appreciated, therefore, that it is a simple matter for the user of the clamp to place an object between the jaws of the clamp when they are in their open position and then simply to depress the lever 18 with his thumb to secure the object in proper position.

The clamp can be mounted on a frame or other support at any desired location by means of clamp 32 which operates on a principle similar to that used in the previously described clamp. Thus, the clamp 32 comprises a first elongated member 34 pivoted to the base portion 10 at 36, a second elongated member 38 pivoted to the first elongated member 34 at 40 and to an L-shaped movable jaw 42 at 44, and a lever 46 which is integral with the second elongated member 38. The L-shaped movable jaw 42 is pivoted to the base portion 10 at 48, and the base portion 10 itself functions as the fixed jaw of the clamp. With this mechanism again it is a simple matter for the user of the device to depress the lever 46 to secure the clamp in its desired position on the frame or other support.

As shown, one or both of the jaws may have a padded surface, as at 50, so as to adjust to different thicknesses of the object to be held. Also, the lips of the jaws may be extended towards each other, as at 52, to positively prevent motion of an object held by the jaws in the direction perpendicular to the base portion 10.

Preferably the levers 18, 46 are formed integrally with the elongated members 20, 38, as shown, and preferably the elongated members 24, 34 abut the base portion 10 and the levers 18, 46 abut the elongated members 24, 34 when the movable jaws 14, 42 are in their closed position. As will be readily appreciated, the latter design feature adds immensely to the strength of the device.

What I claim as my invention is:

1. A clamp comprising:
   (a) a base (10);
   (b) a jaw (12) fixedly mounted on said base (10) and extending upwardly therefrom;
   (c) an opposing jaw (14) spaced along said base (10) from said fixed jaw (12) and in clamping relation to said fixed jaw (12) when said clamp is in its closed position, said opposing jaw (14) being pivotally mounted (16) at one end to said base (10); and
   (d) clamp opening and closing means for moving said opposing jaw (14) into and out of clamping relation to said fixed jaw (12) by pivoting and opposing jaw (14) on said opposing jaw's base pivot mounting (16), said means comprising:

(i) a first elongated member (24) pivotally mounted (30) at a first end remote from said jaws (12 and 14) on said base (10) and free of said base at its second end proximate to said jaws, said first elongated member (24) being parallel to said base (10) when said jaws are in the closed position;

(ii) a lever (18) pivotally mounted (28) on said first member (24) at said second end of said first member (24); and (iii) a second elongated member (20) extending from said lever's pivot (28) at said second end of said first elongated member (24) angularly to the end of said opposing jaw (14) remote from said base (10) whereat said second elongated member (20) is pivotally connected (26) to said opposing jaw (14), whereby said opposing jaw (14) can be pivoted out of clamping relationship with said fixed jaw (12) by actuation of said lever (18) resulting in over-center motion of the pivot point (18) of said lever (18) at said second end of said first elongated member (24).

2. A clamp as recited in claim 1 and further comprising lips (52) formed on the ends of said jaws (12 and 14) remote from said base (10), said lips being in face-opposing relation.

3. A clamp as recited in claim 1 and further comprising means (32) for securing said clamp to a support frame.

4. A clamp as recited in claim 3 wherein said means for securing said clamp to a support frame comprises a knee linkage (34, 36, 38, 40, 44) actuated by a lever (46).

5. A clamp comprising:
(a) a base (10);
(b) a first elongated member (34) pivotally mounted (36) at a first end thereof on said base (10) and free of said base (10) at its second end, said first elongated member (34) being parallel to said base (10) when said clamp is in its closed position;
(c) a second elongated member (38) pivotally mounted (40) on said first elongated member (34) at said second end of said first member (34); and
(d) a movable jaw (42) pivotally connected (44 and 48) to said second elongated member (38) and to said base (10), the working portion of said movable jaw (42) being parallel to said base (10) when said clamp is in its closed position, whereby said movable jaw (42) can be pivoted out of parallel with said base (10) by actuation of said elongated members (34, 38), resulting in over-center motion of the pivot point (40) of said second elongated member (38) at said second end of said first elongated member (34).

6. A clamp as recited in claim 5 wherein said movable jaw (42) has a padded surface (50) facing said base (10) so as to adjust to different thicknesses of support frames to which said clamp is to be secured and to give a secure grip thereon.

7. A clamp comprising:
(a) a base (10);
(b) a jaw (12) fixedly mounted on said base (10) and extending upwardly therefrom;
(c) an opposing jaw (14) spaced along said base (10) from said fixed jaw (12) and in clamping relation with said fixed jaw (12) when said clamp is in its closed position, said opposing jaw (14) being pivotally mounted (16) at one end to said base (10); and
(d) clamp opening and closing means for moving said opposing jaw (14) into and out of clamping relation with said fixed jaw (12) by pivoting said opposing jaw (14) on said opposing jaw's base pivot mounting (16), said means comprising a knee linkage (22) actuated by a lever (18).

8. A clamp comprising:
(a) a base (10);
(b) a jaw (12) fixedly mounted on said base (10) and extending upwardly therefrom;
(c) an opposing jaw (14) spaced along said base (10) from said fixed jaw (12) and in clamping relationship to said fixed jaw (12) when said clamp is in its closed position, said opposing jaw (14) being pivotally mounted (16) at one end to said base (10); and
(d) clamp opening and closing means for moving said opposing jaw (14) into and out of clamping relation with said fixed jaw (12) by pivoting said opposing jaw (14) on said opposing jaw's base pivot mounting (16), said means comprising an elongated member (20, 24) pivotally connected to said opposing jaw (14) at one end (26) and to said base (10) at the other (30), said elongated member (20, 24) being capable of flexure intermediate its ends (28), whereby said opposing jaw, (14), said elongated member (20, 24), and a portion of said base (10) constitute a deformed triangle when the clamp is closed the vertices (16, 26, 30) of which are pivot points and one side of which is deformed in one direction when the clamp is open.

9. A clamp is recited in claim 8 wherein said one side of said deformed triangle is deformed inwardly when the clamp is closed and outwardly when the clamp is open.

10. A clamp comprising a base (10), a first jaw (12) fixed to said base (10) and extending upwardly therefrom, a second jaw (14) opposite said first jaw (12) and pivotally mounted (16) at its lower end on said base (10) so as to be movable toward and away from said first jaw (12), and means for opening and closing said jaws (12, 14) by moving said second jaw (14) into and out of clamping relationship with said first jaw (12), said means comprising:
(a) a hinge member (24) pivotally mounted (30) on said base (10) at a first end thereof remote from said second jaw (14) and adapted to lie parallel to said base (10) when said clamp is closed;
(b) a lever (18) pivotably mounted (28) on said hinge member (24) at a second end of said hinge member; and
(c) elongated member (20) extending from said lever's pivot (28) angularly to said second jaw (14) whereat said elongated member (20) is pivotably connected (26), whereby said hinge member (24) is pivoted out of parallel relationship with said base (10) by actuation of said lever (18) which in turn causes said second jaw (14) to be pivoted out of its clamping position.

11. A clamp comprising:
(a) a base (10);
(b) a vise-like jaw (14) pivotally mounted on said base (10) for holding an object to be clamped;
(c) a clamp opening and closing means for pivoting said jaw (14) on said base (10), said means comprising:
(i) a first elongated member (24) pivotally mounted (30) at a first end remote from said jaw (14) on said base (10) and free of said base (10) at its second end proximate to said jaw (14);

(ii) a lever (18) pivotally mounted (28) on said first member (24) at said second end of said first member (24); and (iii) a second elongated member (20) extending from said lever's pivot (28) at said second end of said first elongated member (24) to the end of said jaw (14) remote from said base (10), whereat said second elongated member (20) is pivotally connected (26) to said jaw (14), whereby said jaw (14) can be pivoted on said base (10) by actuation of said lever (18), resulting in over-center motion of the pivot point (28) of said lever (18) at said second end of said first elongated member (24).

12. A clamp as recited in claim 11 wherein said first elongated member (24) is parallel to and lies against said base (10) when said jaw (14) is in its closed position and wherein said jaw comprises a generally planar clamping surface extending substantially the width of said base.

13. A clamp comprising:
    (a) a base (10);
    (b) a first elongated member (34) pivotally mounted (36) at a first end thereof on said base (10) and free of said base (10) at its second end;
    (c) a second elongated member (38) pivotally mounted (40) on said first elongated member (34) at said second end of said first member (34); and
    (d) a movable jaw (42) pivotally connected (44 and 48) to said second elongated member (38) and to said base (10), whereby said movable jaw (42) can be pivoted by actuation of said elongated member (34 and 38), resulting in over-center motion of the pivot point (40) of said second elongated member (38) at said second end of said first elongated member (34).

14. A clamp as recited in claim 13 wherein said first elongated member (34) is parallel to and lies against said base (10) when said movable jaw (42) is in its closed position.

15. A clamp as recited in claim 13 wherein the working portion of said movable jaw (42) is parallel to said base (10) when said clamp is in its closed position.

16. A clamp comprising:
    (a) a base (10);
    (b) a jaw (42) pivotally mounted on said base (10); and
    (c) clamp opening and closing means for pivoting said jaw (42) on said base (10), said means comprising a knee linkage (34 and 38) actuated by a lever (46).

17. A clamp as recited in claim 16 wherein the working portion of said jaw (42) is parallel to said base (10) when said clamp is in its closed position.

18. A clamp comprising:
    (a) a base (10);
    (b) a vise-like jaw (14) pivotally mounted on said base (10) for holding an object to be clamped;
    (c) clamp opening and closing means for pivoting said jaw (14) on said base (10), said means comprising an elongated member (20 and 24) pivotally connected to said jaw (14) at one end (26) and to said base (10) at the other end (30), said elongated member (20 and 24) being capable of flexure intermediate its ends (28), whereby said jaw (14), said elongated member (20 and 24), and a portion of said base (10) constitute a deformed triangle when the clamp is closed, the vertices (16, 26, 30) of which are pivot points and one side of which is deformed in one direction when the clamp is closed and in the other direction when the clamp is open.

19. A clamp as recited in claim 18 wherein said one side of said deformed triangle is deformed inwardly when the clamp is closed and outwardly when the clamp is open.

20. A clamp comprising:
    (a) a base (10);
    (b) means (12) rigidly attached to said base for abutting an article to be clamped;
    (c) a vise-like jaw (14) pivotally mounted on said base (10) for holding an object to be clamped;
    (d) clamp opening and closing means for pivoting said jaw (14) on said base (10) for clamping an article between said abutting means and said jaw, said clamp opening and closing means comprising:
        (i) a hinge member (24) pivotally mounted (30) on said base (10) at a first end thereof remote from said jaw (14);
        (ii) a lever (18) pivotally mounted (28) on said hinge member (24) at a second end of said hinge member (24); and
        (iii) an elongated member (20) of said lever (18) extending from said lever's pivot (28) to said jaw (14), whereat said elongated member (20) is pivotally connected (26), whereby said hinge member (24) is pivoted relative to said base (10) by actuation of said lever (18), which in turn causes said jaw (14) to be pivoted out of its clamping position.

21. A clamp as recited in claim 20 wherein said hinge member (24) is parallel to and lies against said base (10) when said jaw (14) is in its closed position.

* * * * *